United States Patent
Plessis et al.

(10) Patent No.: US 7,875,737 B2
(45) Date of Patent: Jan. 25, 2011

(54) PYRAN DERIVATIVES, PROCESS OF PREPARATION AND USE THEREOF IN PERFUMERY AND FLAVOURING

(75) Inventors: Caroline Plessis, Bar sur Loup (FR); Jean Mane, Grasse (FR)

(73) Assignee: V. Mane Fils, Bar-sur-Loup (FR)

( * ) Notice: Subject to any disclaimer, the term of this patent is extended or adjusted under 35 U.S.C. 154(b) by 536 days.

(21) Appl. No.: 11/948,176

(22) Filed: Nov. 30, 2007

(65) Prior Publication Data
US 2008/0138297 A1 Jun. 12, 2008

Related U.S. Application Data

(60) Provisional application No. 60/861,966, filed on Dec. 1, 2006.

(51) Int. Cl.
C07D 309/00 (2006.01)
C07D 315/00 (2006.01)
(52) U.S. Cl. .................. 549/423; 549/356
(58) Field of Classification Search .......... 549/423, 549/356
See application file for complete search history.

(56) References Cited

U.S. PATENT DOCUMENTS

| | | | |
|---|---|---|---|
| 2,452,977 | A | 11/1948 | Williams |
| 3,681,263 | A | 8/1972 | Van Der Linde |
| 4,962,090 | A | 10/1990 | Sprecker et al. |
| 4,963,285 | A | 10/1990 | Sprecker et al. |

FOREIGN PATENT DOCUMENTS

| | | |
|---|---|---|
| CH | 655 932 | 5/1986 |
| EP | 0 189 144 | 7/1986 |
| EP | 0 746 552 | 6/2002 |
| FR | 1 013 862 | 8/1952 |
| JP | 52-7911 | 1/1977 |
| WO | WO 2004/009749 | 1/2004 |

OTHER PUBLICATIONS

Ishikawa et al DN 87:135063 (1975) RN 63387-23-5.*
Paul et al DN 52:56155 (1952) RN 100052-47-2.*
Shuikin et al DN 60:23257 (1963) RN 55962-00-0.*

Mikami et al., "Intermolecular Oxonium—Ene Reaction: a New Entry to Stereocontrolled Synthesis of Tetrahydropyrans", J. Chem. Soc. Chem. Commun., 1993, p. 1843-1844, XP-000944733.
Montaudon et al., "Intramolecular hemolytic substitutions", abstract, XP-002430735 retrieved from STN, Database accession No. 1991:247078, vol. 28, No. 2, 1991.
XP-002430734 retrieved from STN, Database Accession No. 1977:535063, abstract JP 52-7911.
XP-002430741 retrieved from STN, Database Accession No. 1977:15605, abstract, JP 52-7911.

* cited by examiner

*Primary Examiner*—Janet L. Andres
*Assistant Examiner*—Raymond Covington
(74) *Attorney, Agent, or Firm*—Young & Thompson

(57) ABSTRACT

Pyran derivatives of general formula (I)

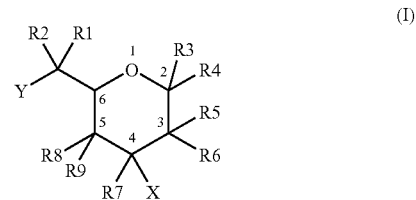

wherein
Y is a 5-, 6- or 7-membered ring, preferably a 5-membered ring, methyl or ethyl mono- or polysubstituted, and optionally unsaturated, and R1, R2, R3, R4 are, each independently, a hydrogen atom or a linear or branched $C_{1-5}$ alkyl or $C_{2-5}$ alkenyl group, and X is present or absent; when X is present, R5, R6, R7, R8, R9 are all present, and X is a hydrogen atom or an OZ group, wherein Z is a hydrogen atom or a R10 group or a C(O)R10 group; when X is absent, a double bond involving the carbon atom at the 4 position is present and R7, R8 and R9 are present, and one of R5 or R6 is present and the other one is absent, or R5, R6, and R7 are present, and one of R8 or R9 is present and the other one is absent, or R7 is a =C(R11)(R12) group and R5, R6, R8, R9 are present; and when they are present, each of R5-R12 group is, independently, a hydrogen atom or a linear or branched $C_{1-5}$ alkyl or $C_{2-5}$ alkenyl group; and use of at least one pyran derivative of formula (I) as flavoring or fragrant agent.

8 Claims, No Drawings

PYRAN DERIVATIVES, PROCESS OF PREPARATION AND USE THEREOF IN PERFUMERY AND FLAVOURING

The present invention relates to the field of fragrances and flavours. More particularly, the invention relates to pyran derivatives, the process of preparation thereof, and their use in the field of perfumery and flavouring.

The terms "fragrance" and "fragrant", as used herein, are used interchangeably whenever a compound or a mixture of compounds is referred to, which is intended to pleasantly stimulate the sense of smell.

The terms "flavour", and "flavouring", as used herein, are used interchangeably whenever a compound or a mixture of compounds is referred to, which is intended to stimulate the sense of taste and smell. Also in the meaning of the invention, the term flavouring relates to the flavouring of any liquid or solid, human or animal, in particular of drinks, dairy products, ice creams, soups, sauces, dips, dishes, meat products, culinary assistances, salted biscuits or snacks. It also means the flavouring of beers, wines and tobaccos.

The term "organoleptic compound", such as for example fragrances and flavours, as used herein, refers to compounds of the invention which stimulate the sense of smell or taste, and are thus perceived as having a characteristic odour and/or flavour.

By the term "masking" is meant reducing or eliminating malodour or bad flavour perception generated by one or more molecules entering in the composition of a product.

The term "isomer", in the present invention, means molecules having the same chemical formula, which means same number and types of atoms, but in which the atoms are arranged differently. The term "isomer" includes structural isomers, geometric isomers, optical isomers and stereoisomers.

The term "alkyl" or "alkyl group", in the present invention, means any linear or branched saturated hydrocarbon chain, having preferably 1, 2, 3, 4 or 5 carbon atoms and herein referred to as $C_{1-5}$ alkyl group, such as for example methyl, ethyl, propyl, isopropyl, butyl, t-butyl, pentyl.

The term "alkenyl" or "alkenyl group", in the present invention, means any linear or branched mono or poly unsaturated hydrocarbon chain, having preferably 2, 3, 4 or 5 carbon atoms and herein referred to as $C_{2-5}$ alkenyl group, such as for example ethenyl, propenyl, butenyl, or pentenyl.

The term "cycloalkyl" or "cycloalkyl group", in the present invention, means any cyclic saturated hydrocarbon chain having preferably 5, 6 or 7 carbon atoms, such as for example cyclopentyl, cyclohexyl and cycloheptyl, substituted or not by an alkyl or alkenyl group as described above.

The term "cycloalkenyl" or "cycloalkenyl group", in the present invention, means any cyclic mono or poly unsaturated hydrocarbon chain having preferably 5, 6 or 7 carbon atoms, such as for example cyclopentenyl, cyclohexenyl and cycloheptenyl, substituted or not by an alkyl or alkenyl as described above.

The term "cycloalkylacetaldehyde", in the present invention, represents an acetaldehyde substituted by a cycloalkyl group.

The term "cycloalkenylacetaldehyde", in the present invention, represents an acetaldehyde substituted by a cycloalkenyl group.

Tetrahydropyran and dihydropyran derivatives belong to an important class of fragrant ingredients and a large work has already been done to prepare known compounds, such as for example Rose Oxide and similar derivatives, from linear or branched alkyl and alkenyl aldehydes, as described in U.S. Pat. No. 3,681,263 and in WO 04/009749, or from benzylic aldehydes as described in CH 655 932.

Similarly, esters or ethers of pyranols have been found of interest in the aromatic industry as shown in U.S. Pat. No. 4,963,285, U.S. Pat. No. 4,962,090.

U.S. Pat. No. 2,452,977 relates to a process for the production of cyclic compounds; according to this process, an unsaturated alcohol is reacted with an aldehyde to produce a cyclic compound having an oxygen atom within the ring. Some resulting compounds are pyrans.

The need of new compounds is of great importance for the development of the flavour and fragrance industry, which recently had to face stricter international regulatory requirements about the use of certain materials, as well as environmental concerns and customer demands for improved performance. Being able of manufacturing new fragrant compounds is therefore a challenge.

When exploring further the pyran derivatives in order to identify new fragrant compounds, the Applicant focused on lateral cyclic chains, more specifically on cycloalkylacetaldehydes and cycloalkenylacetaldehydes as starting materials.

None of the above-cited document mentions nor suggests a possible use of cycloalkylacetaldehyde or cycloalkenylacetaldehyde to prepare pyran derivatives, and of course, as the resulting pyran derivatives are new, there is no prior art information regarding their possible olfactive or organoleptic properties.

This invention thus relates to pyran derivatives of general formula (I)

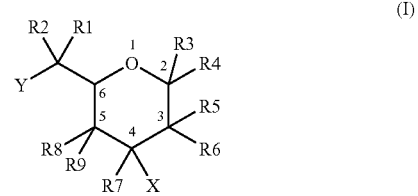

(I)

wherein
- Y is a 5-, 6- or 7-membered ring, preferably a 5-membered ring, optionally methyl or ethyl mono- or polysubstituted, and optionally unsaturated, and
- R1, R2, R3, R4 are, each independently, a hydrogen atom or a linear or branched $C_{1-5}$ alkyl or $C_{2-5}$ alkenyl group, and
- X is present or absent,
- when X is present,
  - R5, R6, R7, R8, R9 are all present, and X is a hydrogen atom or an OZ group, wherein Z is a hydrogen atom or a R10 group or a C(O)R10 group
- when X is absent, a double bond involving the carbon atom at the 4 position is present and
  - R7, R8 and R9 are present, and one of R5 or R6 is present and the other one is absent, or
  - R5, R6, and R7 are present, and one of R8 or R9 is present and the other one is absent, or
  - R7 is a =C(R11)(R12) group and R5, R6, R8, R9 are present,
- and when they are present, each of R5-R12 group is, independently, a hydrogen atom or a linear or branched $C_{1-5}$ alkyl or $C_{2-5}$ alkenyl group.

Preferably, Y is a 5-, 6- or 7-membered ring methyl or ethyl mono- or polysubstituted, optionally unsaturated.

According to an embodiment, preferred pyran derivatives of the invention are of general formula (I) wherein Y is a 5-membered ring, said ring being saturated or including one double bond, said ring being optionally methyl or ethyl mono- or polysubstituted, preferably Y=

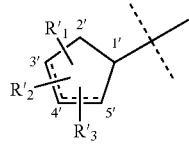

wherein R'1, R'2 and R'3 are each independently a hydrogen atom or a methyl group or an ethyl group, at least one of R'1, R'2 and R'3 being a methyl or an ethyl group, wherein the dotted lines represent a double bond and is present or not.

R1, R2, R3, R4 are, each independently, a hydrogen atom or a linear or branched $C_{1-5}$ alkyl or $C_{2-5}$ alkenyl group, and X is present or absent, when X is present, R5, R6, R7, R8, R9 are all present, and X is a hydrogen atom or an OZ group, wherein Z is a hydrogen atom or a R10 group or a C(O)R10 group when X is absent, a double bond involving the carbon atom at the 4 position is present and R7, R8 and R9 are present, and one of R5 or R6 is present and the other one is absent, or R5, R6, and R7 are present, and one of R8 or R9 is present and the other one is absent, or R7 is a =C(R11)(R12) group and R5, R6, R8, R9 are present, and when they are present, each of R5-R12 group is, independently, a hydrogen atom, or a linear or branched $C_{1-5}$ alkyl or $C_{2-5}$ alkenyl group.

In a specific embodiment, the invention relates to pyran derivatives of general formula (I) as described above, wherein Y is one of a (Y1), (Y2), (Y3) or (Y4) group

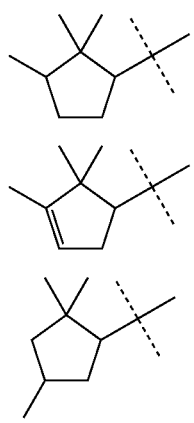

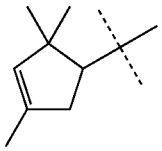

R1, R2, R3, R4 are, each independently, a hydrogen atom, a linear or branched $C_{1-5}$ alkyl or $C_{2-5}$ alkenyl group, and X is present or absent, when X is present, R5, R6, R7, R8, R9 are all present, and X is a hydrogen atom or an OZ group, wherein Z is a hydrogen atom or a R10 group or a C(O)R10 group when X is absent, a double bond involving the carbon atom at the 4 position is present and R7, R8 and R9 are present, and one of R5 or R6 is present and the other one is absent, or R5, R6, and R7 are present, and one of R8 or R9 is present and the other one is absent, or R7 is a =C(R11)(R12) group and R5, R6, R8, R9 are present, and when they are present, each of R5-R12 group is, independently, a hydrogen atom, a linear or branched $C_{1-5}$ alkyl or $C_{2-5}$ alkenyl group.

In another embodiment, preferred pyran derivatives of general formula (I) as described above, are those wherein Y is a 5-, 6- or 7-membered ring, preferably a 5-membered ring, optionally methyl or ethyl mono- or polysubstituted, and optionally unsaturated, or Y is a (Y1), (Y2), (Y3), (Y4) group, one of R3 or R4 is an hydrogen atom, and the other one is a methyl group R7 is a =CH₂ group and X is absent; or R7 is a methyl group and X is present or absent; when R7 is a methyl group and X is present, X is an hydrogen atom or an OZ group, wherein Z is an hydrogen atom or a R10 group or a C(O)R10 group; when R7 is a methyl group and X is absent, a double bond involving the carbon atom at the 4 position is present and R8 and R9 are present, and one of R5 or R6 is present and the other one is absent, or R5, R6, are present, and one of R8 or R9 is present and the other one is absent, R1, R2 and R10 are each independently a hydrogen atom, or a linear or branched $C_{1-5}$ alkyl or $C_{2-5}$ alkenyl group When present, R5, R6, R8, R9 are each a hydrogen atom.

In still another embodiment, preferred pyran derivatives of general formula (I) as described above, are selected in the group comprising 4-methylene-2-(2,2,3-trimethyl-cyclopent-3-enylmethyl)-tetrahydropyran, 4-methyl-6-(2,2,3-trimethyl-cyclopent-3-enylmethyl)-3,6-dihydro-2H-pyran, 4-methyl-2-(2,2,3-trimethyl-cyclopent-3-enylmethyl)-3,6-dihydro-2H-pyran, 4-methyl-2-(2,2,3-trimethyl-cyclopentylmethyl)-tetrahydropyran, 4-methylene-2-(2,2,3-trimethyl-cyclopentylmethyl)-tetrahydropyran, 4-methyl-6-(2,2,3-trimethyl-cyclopentylmethyl)-3,6-dihydro-2H-pyran, 4-methyl-2-(2,2,3-trimethyl-cyclopentylmethyl)-3,6-dihydro-2H-pyran, 4-methyl-4-(3-methyl-but-3-enyloxy)-2-(2,2,3-trimethyl-cyclo-pentylmethyl)-tetrahydropyran.

According to another embodiment, pyran derivatives of the invention are of general formula (I) wherein Y is a 5-, 6-, or 7-membered ring, optionally methyl or ethyl mono or polysubstituted, and saturated; or Y is a 5- or 7-membered ring, optionally methyl or ethyl mono or polysubstituted, and polyunsaturated; or Y is a 5- or 6-membered ring, optionally methyl or ethyl mono or polysubstituted, mono or di-unsaturated, provided that the double bond is not in position 1', or Y is a 7-membered ring, optionally methyl or ethyl mono or polysubstituted, mono-unsaturated, or R1, R2, R3, R4 are, each independently, a hydrogen atom or a linear or branched $C_{1-5}$ alkyl or $C_{2-5}$ alkenyl group, and X is present or absent, when X is present, R5, R6, R7, R8, R9 are all present, and X is a hydrogen atom or an OZ group, wherein Z is a hydrogen atom or a R10 group or a C(O)R10 group when X is absent, a double bond involving the carbon atom at the 4 position is present and R7, R8 and R9 are present, and one of R5 or R6 is present and the other one is absent, or R5, R6, and R7 are present, and one of R8 or R9 is present and the other one is absent, or R7 is a =C(R11)(R12) group and R5, R6, R8, R9 are present, and when they are present, each of R5-R12 group is, independently, a hydrogen atom, or a linear or branched $C_{1-5}$ alkyl or $C_{2-5}$ alkenyl group.

In a second aspect, the invention relates to a process for the preparation of the pyran derivatives of the invention, said process being characterized in that a compound of general formula (A)

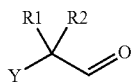
(A)

wherein

Y is a 5-, 6- or 7-membered ring, preferably a 5-membered ring, optionally methyl or ethyl mono- or polysubstituted, and optionally unsaturated, R1 and R2 are, each independently, a hydrogen atom or a linear or branched $C_{1-5}$ alkyl or $C_{2-5}$ alkenyl group, is reacted, in presence of an acid, with a compound of general formula (B)

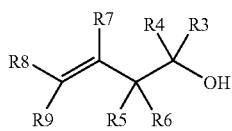
(B)

wherein

R3, R4, R5, R6, R7, R8 and R9 are, each independently, a hydrogen atom or a linear or branched $C_{1-5}$ alkyl group, or a linear or branched $C_{2-5}$ alkenyl group.

According to an embodiment of the invention, the process further comprises a step to convert the aldehyde (A) into an acetal of general formula (C)

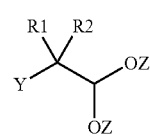
(C)

wherein.

Y is a 5-, 6- or 7-membered ring, preferably a 5-membered ring, optionally methyl or ethyl mono- or polysubstituted, and optionally unsaturated, R1, R2, are, each independently, a hydrogen atom, a linear or branched $C_{1-5}$ alkyl or $C_{2-5}$ alkenyl group, Z is a R10 group wherein R10 is a linear or branched $C_{1-5}$ alkyl or $C_{2-5}$ alkenyl group, prior to the reaction with the alcohol (B).

According to an embodiment, (A) and/or (B) and/or (C) is used as an optically pure isomer.

In another embodiment, the invention relates to the process as described above, wherein compound (A) or compound (C) is reacted, in presence of an acid, with compound (B), and from the resulting mixture, the different compounds of formula (I), wherein X is OZ, Z being a hydrogen atom or a linear or branched $C_{1-5}$ alkyl or $C_{2-5}$ alkenyl group, or wherein X is absent, are separated.

According to another embodiment of the invention, compound (A) is reacted with compound (B), in presence of an acid, and from the resulting mixture, the compounds of formula (I), wherein X is OH, are separated from the compounds of formula (I) wherein X is absent, and then subjected to an esterification reaction, in order to obtain compounds of formula (I) wherein X is OC(O)R10.

The esterification reaction may be performed by usual procedures known by one skilled in the art.

According to another embodiment of the invention, compound (A) is reacted with compound (B), in presence of an acid, and from the resulting mixture, the compounds of formula (I), wherein X is OH, are separated from the compounds of formula (I), wherein X is absent and then subjected to an alkylation reaction in order to obtain compounds of formula (I) wherein X is OZ, Z being a linear or branched $C_{1-5}$ alkyl or $C_{2-5}$ alkenyl group.

The alkylation reaction may be performed by usual procedures known by one skilled in the art.

In another particular embodiment, the invention relates to the process as described above, wherein compound (A) is reacted with compound (B) and the resulting mixture of pyran derivatives is subjected to a dehydration reaction in presence of an acid, said process resulting in the manufacturing of compounds of formula (I) wherein X is absent, and a double bond at the 4 position is present.

Separation steps may be performed by any techniques known from one skilled in the art.

Another aspect of the invention is a composition comprising at least one compound of formula (II), and/or at least one compound of general formula (III) and/or at least one compound of general formula (IV), and optionally (V) and/or (VI)

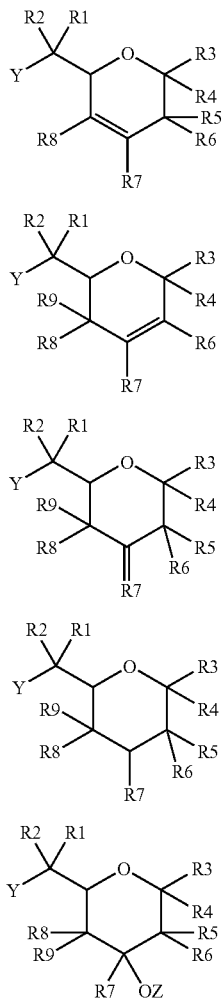

wherein
- Y is a 5-, 6- or 7-membered ring, preferably a 5-membered ring, optionally methyl or ethyl mono- or polysubstituted, and optionally unsaturated,
- R1, R2, R3, R4, R5, R6, R7, R8, R9 are, each independently, a hydrogen atom, a linear or branched $C_{1-5}$ alkyl or $C_{2-5}$ alkenyl group,
- Z is a hydrogen atom or a linear or branched $C_{1-5}$ alkyl or $C_{2-5}$ alkenyl group or a group C(O)R10 wherein R10 is a linear or branched $C_{1-5}$ alkyl or $C_{2-5}$ alkenyl group.

This invention relates to the compounds of formula (I), as described above, but also to any of their various isomers.

In a last aspect, the invention relates to the use of the compounds of formula (I) as described above.

In a first embodiment, the invention relates to the use of at least one compound or of the composition as described above, in the perfumery field for the preparation of perfumed bases and concentrates, fragrances, perfumes and similar products; topic compositions; cosmetic compositions such as for example face and body creams, cleansers, facial treatments, talc powders, hair oils, shampoos, hair lotions, bath oils and salts, shower and bath gels, soaps, body anti-perspirants and deodorizers, pre-shave, shaving and post-shave creams and lotions, creams, toothpastes, mouth baths, pomades; cleaning products, such as for example softeners, detergents, air deodorizers and household cleaning supplies. Therefore, the invention also relates to a fragrant composition including at least one compound of formula (I) or one or more isomers of a compound of formula (I).

In a second embodiment, the invention relates to the use of at least one compound or of the composition as described above, as flavouring agents for the preparation of flavouring compositions or articles, such as for example drinks, dairy products, ice creams, soups, sauces, dips, dishes, meat products, culinary assistances, salted biscuits or snacks and also beers, wines and tobaccos. Therefore, the invention also relates to a flavoured composition including at least one compound of formula (I) or one or more isomers of a compound of formula (I).

In a third embodiment, the invention relates to the use of the compounds or composition as described above, as masking agents of odours and/or flavours, and to any pharmaceutical, cosmetic or food composition containing at least one compound of formula (I) or one or more isomers of a compound of formula (I). Therefore, this invention also relates to any composition comprising at least one compound of formula (I), as herein described, in combination with any suitable excipient, especially pharmaceutical or cosmetic or dietary excipient.

The compounds of the invention may be used alone or in combination with other perfuming or flavouring ingredients, solvents, additives or fixatives, commonly used and that the man skilled in the art is able to choose in regard of the desired effect and the nature of the product to perfume or flavour. This invention includes, for example, any composition comprising one or more isomers of a compound of formula (I). According to a preferred embodiment, this invention relates to a composition comprising at least two or three isomers of a compound of formula (I).

In another embodiment, in the uses as described above, the compounds of the invention are used in a concentration comprised in a range from 0.001% to 99% in weight, in particular from 0.1% to 50% in weight, more particularly from 0.1% to 30% in weight. It is known by the man skilled in the art that these values depend on the nature of the composition/article to be perfumed and/or flavoured, the desired intensity of the perfume and/or flavour, and the nature of the other ingredients present in said composition or article. According to a preferred embodiment, the compounds of the invention are used in an olfactory effective amount. By olfactory effective amount is meant a level or amount of fragrant/flavouring compound in a material at which the incorporated compound exhibits a sensory effect.

Following examples detail the preparation processes of the compounds of the invention and their use. These examples are presented with an only goal of illustration and shall not be regarded as limiting the scope of the invention.

EXAMPLE 1

Preparation of 4-Methylene-2-(2,2,3-trimethyl-cyclopent-3-enylmethyl)-tetrahydro-pyran (A)

4-Methyl-6-(2,2,3-trimethyl-cyclopent-3-enylmethyl)-3,6-dihydro-2H-pyran (B)

4-Methyl-2-(2,2,3-trimethyl-cyclopent-3-enylmethyl)-3,6-dihydro-2H-pyran (C)

A mixture of 1 equivalent of campholenaldehyde and 2 equivalents of 3-methyl-3-buten-1-ol in toluene, with catalytic amount of PTSA, is heated under reflux to remove the formed water. After completion of the reaction (3 hours), the mixture is cooled down and diluted with toluene. After washing with a saturated bicarbonate solution and brine, the organic phase is dried over MgSO$_4$, filtered and the solvents are evaporated to afford a crude oil.

The distilled product (82° C./0.8 torr) consists in a mixture of isomers (A), (B) and (C) in a 27:16:57 ratio.

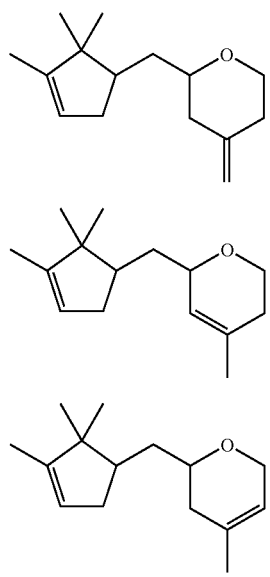

Its odour is powerful, hesperidic (bitter orange, petitgrain), green (galbanum, peas).

The different isomers are obtained separately by a fine fractionation distillation with a packed column under partial reflux.

Each isomer is a mixture of 2 diastereoisomers.

$^1$H-NMR (CDCl$_3$, 200 MHz): common protons δ (ppm) 0.75 (s, 3H), 0.97 (s, 3H), 1.25-2.5 (m, 7H), 1.59 (s, 3H), 5.22 (m, 1H).

Characteristic Protons:

(A) δ (ppm) 1.25-2.5 (m, 2H), 3.2-3.7 (m, 3H), 4.7 (m, 2H).

(B) δ (ppm) 1.68 (s, 3H), 3.9-4.2 (m, 3H), 5.32 (m, 1H).

(C) δ (ppm) 1.68 (s, 3H), 3.2-3.7 (m, 1H), 3.9-4.2 (m, 2H), 5.4 (m, 1H).

IR (film, cm$^{-1}$): 796 m, 1014 m, 1095 m, 1122 s, 1138 m, 1360 m, 1382 m, 1437 m, 1445 m, 1463 m, 2864 s, 2930 s, 2955 s.

MS [e/m (%)]: 220 (M+, 12), 149(5), 135(4), 119(8), 108 (100), 93(59), 79(19), 67(35), 53(20), 41(48).

EXAMPLE 2

Preparation of 4-methyl-2-(2,2,3-trimethyl-cyclopentylmethyl)-tetrahydro-pyran

A mixture of isomers, prepared in example 1, is treated under a normal pressure of hydrogen in ethanol with catalytic amount of palladium on charcoal (5%) to give the desired tetrahydropyran. The crude product obtained after filtration of the reaction mixture on Clarcel® is purified by distillation (88° C./0.7 torr). It consists in four couples of diastereoisomers (2 major and 2 minor, the ratio between them is 36:42:10:12).

Its odour is bitter orange, woody, a bit dusty/musky.

$^1$H-NMR (CDCl$_3$, 200 MHz): common protons δ (ppm) 0.46 & 0.48 (s, 3H), 0.65-0.87 (m, 6H), 0.90-1.30 (m, 4H), 1.30-2.20 (m, 9H), 3.10-3.75 (m, 2H).

Major isomers: Characteristic protons δ (ppm) 0.90 (d, J=6.1 Hz) & 0.91 (d, J=6.2 Hz): 3H; 3.85-4.0 (m, 1H).

Minor isomers: Characteristic protons δ (ppm) 1.01 (d, 1H, J=7.1 Hz) & 1.02 (d, 1H, J=7.1 Hz): 3H; 3.10-3.75 (m, 1H).

$^{13}$C-NMR (CDCl$_3$, 60 MHz):

Major isomers: 13.9 & 14.26, 22.36 & 24.40, 25.37 & 25.46, 28.11 & 28.39, 30.14 & 30.26, 30.27 & 30.41, 34.75 & 34.82, 37.40 & 37.51, 40.21 & 41.87, 42.03 & 42.35, 44.90 & 44.96, 46.11 & 47.01, 67.99 & 68.12, 76.37 & 77.18.

Minor isomers (selected data): 13.90 & 14.26, 18.72 & 19.18, 24.78 & 24.94, 28.0 & 28.32, 32.4 & 32.62, 35.44 & 35.96, 37.19 & 38.82, 44.87, 47.4.

IR (film, cm$^{-1}$): 1095 s, 1177 m, 1366 m, 1374 m, 1386 m, 1456 m, 1466 m, 2838 m, 2869 s, 2926 s, 2952 s.

MS [e/m (%)]: 224 (M+, 1), 99(100), 55(18), 43(19), 41(17).

EXAMPLE 3

Preparation of 4-Methylene-2-(2,2,3-trimethyl-cyclopentylmethyl)-tetrahydro-pyran (A)

4-Methyl-6-(2,2,3-trimethyl-cyclopentylmethyl)-3,6-dihydro-2H-pyran (B)

4-Methyl-2-(2,2,3-trimethyl-cyclopentylmethyl)-3,6-dihydro-2H-pyran (C)

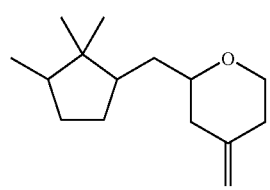

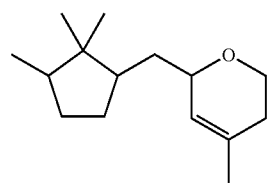

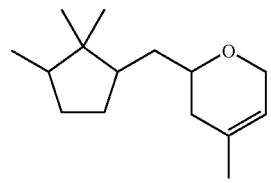

A mixture of isomers (A), (B) and (C) in a 63:14:23 ratio was prepared, according to example 1, starting from hydrogenated campholenaldehyde.

Its odour is similar to that of example 1.

Main Isomers (A):

$^1$H-NMR (CDCl$_3$, 200 MHz): δ (ppm) 0.45-0.55 (m, 3H), 0.75-0.85 (m, 6H), 1.0-1.3 (m, 2H), 1.3-1.55 (m, 3H), 1.55-2.0 (m, 5H), 2.0-2.4 (m, 2H), 3.1-3.4 (m, 2H), 3.9-4.05 (m, 1H), 4.65-4.75 (m, 2H).

$^{13}$C-NMR (CDCl$_3$, 60 MHz): δ (ppm) 13.89 & 14.23, 25.34 & 25.46, 28.04 & 28.43, 30.11 & 30.24, 35.22 & 35.27, 37.20, 40.81 & 42.24, 44.87 & 44.95, 46.05 & 47.07, 46.14 & 46.19, 68.55 & 68.64, 77.63 & 78.54, 108.01 & 108.17, 144.75 & 144.97.

(B) Isomers (Characteristic protons): δ (ppm) 3.9-4.05 (m, 3H), 5.25-5.30 (m, 1H).

$^{13}$C-NMR (CDCl$_3$, 60 MHz, selected data): δ (ppm) 63.12 & 63.44, 72.53 & 72.72, 123.67 & 125.10.

(C) Isomers (Characteristic protons): δ (ppm) 3.4-3.65 (m, 1H), 3.95-4.15 (m, 2H).

$^{13}$C-NMR (CDCl$_3$, 60 MHz, selected data): δ (ppm) 65.76 & 65.84, 73.39 & 73.72, 119.65 & 119.74.

EXAMPLE 4

4-methyl-4-(3-methyl-but-3-enyloxy)-2-(2,2,3-trimethyl-cyclo-pentylmethyl)-tetrahydropyran 4-Methyl-4-(3-methyl-but-3-enyloxy)-2-(2,2,3-trimethyl-cyclopentylmethyl)-tetra-hydropyran was obtained under the conditions used in example 3 and was separated from the other derivatives by fine fractionation.

It consists in a trans/cis (60:40) mixture of isomers.

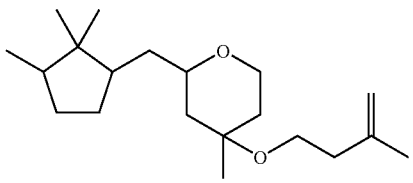

Its odour is not powerful, bitter orange.

Major Diastereoisomers, Trans Isomers:
$^1$H-NMR (CDCl$_3$, 200 MHz): δ (ppm) 0.49 (s, 3H), 0.82 (d, 3H, J=10.1 Hz), 0.83 (s, 3H), 1.0-1.9 (m, 12H), 1.28 (s, 3H), 1.74 (s, 3H), 2.24 (t, 2H, J=7.1 Hz), 3.2-3.5 (m, 2H), 3.50 (t, 2H, J=7.2 Hz), 4.74 (m, 2H).

$^{13}$C-NMR (CDCl$_3$, 60 MHz): δ (ppm) 13.91 & 14.29, 21.12 & 21.34, 23.0, 25.38 & 25.46, 28.08 & 28.25, 30.11 & 30.23, 37.24 & 37.35, 37.4 & 37.49, 38.65, 42.08 & 42.39, 43.11 & 44.41, 44.88 & 44.98, 46.11 & 47.0, 58.95, 65.05 & 65.13, 72.60 & 72.66, 73.79 & 74.74, 111.15, 143.24.

MS [e/m (%)]: 308 (M+, 1), 293(2), 223(23), 109(10), 99(72), 97(10), 69(100), 55(10), 43(11), 41(36).

IR (film, cm$^{-1}$): 642 w, 887 m, 1078 m, 1104 s, 1144 m, 1177 m, 1251 w, 1271 w, 1374 m, 1453 m, 1466 m, 1650 w, 2869 s, 2951 s.

Minor Diastereoisomers, Cis Isomers:
$^1$H-NMR (CDCl$_3$, 200 MHz), selected data: δ (ppm) 0.48 (s, 3H), 1.27 (s, 3H), 3.49 (t, 2H, J=7.2 Hz).

$^{13}$C-NMR (CDCl$_3$, 60 MHz), selected data: δ (ppm) 111.36, 143.39.

MS [e/m (%)]: 308 (M+, 1), 293(9), 223(11), 222(11), 221(37), 112(25), 109(10), 99(26), 97(28), 95(12), 69(100), 55(16), 43(17), 41(50).

IR (film, cm$^{-1}$): 642 w, 887 m, 1078 m, 1104 s, 1144 m, 1177 m, 1251 w, 1271 w, 1374 m, 1453 m, 1466 m, 1650 w, 2869 s, 2951 s.

EXAMPLE 5

Fragrance Composition Containing the (A)/(B)/(C) Mixture Obtained in Example 1

A base perfuming composition was prepared as described from the following ingredients:

| | |
|---|---|
| ABRAC NERYL ACETATE | 5 |
| BENZYL ACETATE | 5 |
| BERGAMYL ACETATE | 70 |
| GERANYL ACETATE | 7 |
| LINALYL ACETATE | 45 |
| TERPENYL ACETATE | 60 |
| ACETYL ISOEUGENOL | 5 |
| PHENYLETHYLALCOHOL | 130 |
| BENZALDEHYDE | 2 |
| ALDEHYDE C10 | 2 |
| CYCLAMEN ALDEHYDE ® | 25 |
| ANISALDEHYDE | 20 |
| VELVIONE ® | 5 |
| GLOBANONE ® | 5 |
| METHYL BENZOATE | 2 |
| CETONE MIEL | 5 |
| ETHYL LINALOL | 100 |
| FLOROL ® | 45 |
| BOIS DE GAIAC ESS. | 2 |
| METHYL DIHYDROJASMONATE | 40 |
| IONONE ALPHA | 30 |
| IONONE BETA | 10 |
| MAYOL ® | 30 |
| METHYL ISOEUGENOL | 2 |
| NEROLINE ® | 15 |
| LINALOL OXIDE | 3 |
| TERPINEOL | 85 |
| TETRAHYDROLINALOL | 30 |
| VANILLINE | 1 |
| ACETOPHENONE 10% DPG | 5 |
| PHENYLACETIC ACID 10% DPG | 2 |
| CITRONELLAL C 10% DPG. | 2 |
| INDOLAROME ® 10% DPG | 5 |
| | 800 |

To this base composition of the honeysuckle type were added 10 parts in weight of the (A)/(B)/(C) mixture of isomers obtained in example 1. The novel composition thus obtained showed a greener note, reminding petit-grain essence, with a light orange blossom undertone. Furthermore, the (A)/(B)/(C) mixture imparts freshness to the composition, those interesting aspects of the new fragrance composition have been appreciated in alcoholic, as well as in a shower gel and in a cream base.

The invention claimed is:
1. A compound of general formula (I)

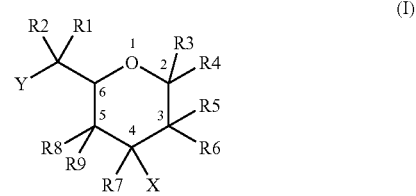

wherein
Y is a 5-membered ring, said ring being saturated or including one double bond, said ring being methyl or ethyl mono- or polysubstituted, R1, R2, R3, R4 are, each independently, a hydrogen atom or a linear or branched $C_{1-5}$ alkyl or $C_{2-5}$ alkenyl group, and X is present or absent, when X is present, R5, R6, R7, R8, R9 are all present, and X is a hydrogen atom or an OZ group, wherein Z is a hydrogen atom or a R10 group or a C(O)R10 group when X is absent, a double bond involving the carbon atom at the 4 position is present and R7, R8 and R9 are present, and one of R5 or R6 is present and the other one is absent, or R5, R6, and R7 are present, and one of R8 or R9 is present and the other one is absent, or R7 is a =C(R11)(R12) group and R5, R6, R8, R9 are present, and when they are present, each of R5—R12 group is, independently, a hydrogen atom or a linear or branched $C_{1-5}$ alkyl or $C_{2-5}$ alkenyl group.

2. The compound of general formula (I) according to claim 1 wherein

Y is one of (Y1), (Y2), (Y3) or (Y4) group

 (Y₁)

 (Y₂)

 (Y₃)

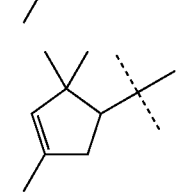 (Y₄)

R1, R2, R3, R4 are, each independently, a hydrogen atom, a linear or branched $C_{1-5}$ alkyl or $C_{2-5}$ alkenyl group, and X is present or absent, when X is present, R5, R6, R7, R8, R9 are all present, and X is a hydrogen atom or an OZ group, wherein Z is a hydrogen atom or a R10 group or a C(O)R10 group when X is absent, a double bond involving the carbon atom at the 4 position is present and R7, R8 and R9 are present, and one of R5 or R6 is present and the other one is absent, or R5, R6, and R7 are present, and one of R8 or R9 is present and the other one is absent, or R7 is a =C(R11)(R12) group and R5, R6, R8, R9 are present, and when they are present, each of R5—R12 group is, independently, a hydrogen atom, a linear or branched $C_{1-5}$ alkyl or $C_{2-5}$ alkenyl group.

3. The compound of general formula (I) according to claim 1, wherein

Y is as previously defined, one of R3 or R4 is a hydrogen atom, and the other one is a methyl group R7 is a =CH2 group and X is absent; or R7 is a methyl group and X is present or absent; when R7 is a methyl group and X is present, X is a hydrogen atom or an OZ group, wherein Z is a hydrogen atom or a R10 group or a C(O)R10 group; when R7 is a methyl group and X is absent, a double bond involving the carbon atom at the 4 position is present and R8 and R9 are present, and one of R5 or R6 is present and the other one is absent, or R5, R6, are present, and one of R8 or R9 is present and the other one is absent, R1, R2 and R10 are, each independently, a hydrogen atom, or a linear or branched $C_{1-5}$ alkyl or $C_{2-5}$ alkenyl group when present, R5, R6, R8, R9 are each a hydrogen atom.

4. The compound of general formula (I) according to claim 1, wherein said compound is selected from the group consisting of: 4-methylene-2-(2,2,3-trimethyl-cyclopent-3-enylmethyl)-tetrahydropyran, 4-methyl-6-(2,2,3-trimethyl-cyclopent-3-enylmethyl)-3,6-dihydro-2H-pyran, 4-methyl-2-(2,2,3-trimethyl-cyclopent-3-enylmethyl)-3,6-dihydro-2H-pyran, 4-methyl-2-(2,2,3-trimethyl-cyclopentylmethyl)-tetrahydropyran, 4-methylene-2-(2,2,3-trimethyl-cyclopentylmethyl)-tetrahydropyran, 4-methyl-6-(2,2,3-trimethyl-cyclopentylmethyl)-3,6-dihydro-2H-pyran, 4-methyl-2-(2,2,3-trimethyl-cyclopentylmethyl)-3,6-dihydro-2H-pyran, and 4-methyl-4-(3-methyl-but-3-enyloxy)-2-(2,2,3-trimethyl-cyclo-pentylmethyl)-tetrahydropyran.

5. A composition comprising at least one compound of formula (II), and/or at least one compound of general formula (III) and/or at least one compound of general formula (IV), and optionally (V) and/or (VI)

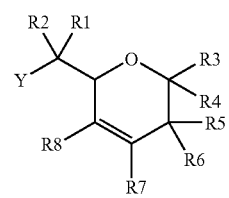 (II)

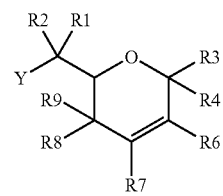 (III)

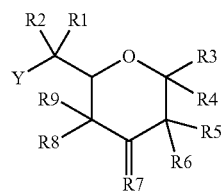 (IV)

-continued

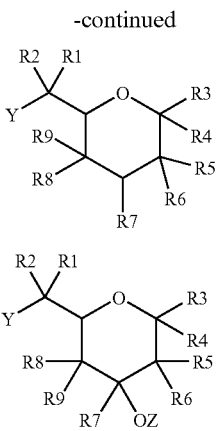

wherein
Y is a 5-, 6- or 7-membered ring, preferably a 5-membered ring, methyl or ethyl mono- or polysubstituted, and optionally unsaturated,
R1, R2, R3, R4, R5, R6, R7, R8, R9 are, each independently, a hydrogen atom, a linear or branched $C_{1-5}$ alkyl or $C_{2-5}$ alkenyl group,
Z is a hydrogen atom or a linear or branched $C_{1-5}$ alkyl or $C_{2-5}$ alkenyl group or a group C(O)R10 wherein R10 is a linear or branched $C_{1-5}$ alkyl or $C_{2-5}$ alkenyl group.

6. The composition according to claim 5, wherein the composition is a fragrant composition selected from the group consisting of:
perfumed bases and concentrates, fragrances, perfumes; topic compositions; cosmetic compositions selected in the group comprising face and body creams, cleansers, facial treatments, talc powders, hair oils, shampoos, hair lotions, bath oils and salts, shower and bath gels, soaps, body anti-perspirants and deodorizers, pre-shave, shaving and post-shave creams and lotions, creams, toothpastes, mouth baths, pomades; cleaning products, selected in the group comprising softeners, detergents, air deodorizers and household cleaning supplies.

7. The composition according to claim 5, wherein the composition is a flavoured composition selected from the group consisting of:
drinks, dairy products, ice creams, soups, sauces, dips, dishes, meat products, culinary assistances, salted biscuits or snacks and also beers, wines and tobaccos.

8. The composition according to claim 5, wherein the composition is a masking agent of odours and/or flavours in a pharmaceutical, cosmetic or food composition.

* * * * *